United States Patent [19]

Yazaki

[11] 4,162,672
[45] Jul. 31, 1979

[54] MAGNETO-THERAPEUTIC DEVICE

[75] Inventor: Seiichi Yazaki, Nara, Japan

[73] Assignee: Fujimoto Company, Limited, Osaka, Japan

[21] Appl. No.: 874,645

[22] Filed: Feb. 2, 1978

[51] Int. Cl.² ............................................ A61N 1/42
[52] U.S. Cl. ................................................ 128/1.3
[58] Field of Search .......................... 128/1.3, 2.06 E

[56] References Cited

U.S. PATENT DOCUMENTS

| 272,904 | 2/1883 | Russell | 128/1.3 |
| 3,610,229 | 10/1971 | Zenkich | 128/2.06 E |

FOREIGN PATENT DOCUMENTS

| 259818 | 5/1963 | Australia | 128/1.3 |
| 445438 | 4/1975 | U.S.S.R. | 128/1.3 |

*Primary Examiner*—William E. Kamm
*Attorney, Agent, or Firm*—Armstrong, Nikaido, Marmelstein & Kubovcik

[57] ABSTRACT

A magneto-therapeutic device comprising an adhesive base sheet, a hard disc-shaped permanent magnet of ferrite adhered to the base sheet in the center of its adhesive face, and a release sheet affixed to the adhesive face of the base sheet except the center portion thereof. The device is useful for curing stiffness in the shoulder and pains in the waist and muscles with its magnetic effects and pressure-stimulation effects.

3 Claims, 6 Drawing Figures

MAGNETO-THERAPEUTIC DEVICE

BACKGROUND OF THE INVENTION

The present invention relates to novel magneto-therapeutic devices, and more particularly to a very convenient magneto-therapeutic device having magnetic effects and pressure-stimulation effects useful for therapeutic purposes.

Therapeutic devices recently proposed for curing stiffness in the shoulder or pains in the waist and muscles include those incorporating metal granules and those utilizing magnetism. The devices of the former type comprise a granule of metal (usually gold or silver because of its resistance to corrosion) having a diameter of about 1 mm. and adhered to an approximately 5 mm. square piece of adhesive plaster. Such devices are affixed to a painful or stiff portion or effective spots of the human body, causing the metal granule to produce a mechanical stimulus on the body for the treatment of stiffness in the shoulder or pain. However, the device of this type has the drawback of failing to achieve a sufficient therapeutic efficacy unless it is held affixed to the body for a prolonged period of time because the granule is extremely small and is therefore unable to give a great stimulus. Additionally the plaster sheet, which is also too small, is inconvenient to handle. Among the magneto-therapeutic devices of the latter type, magnetic bands are well known which are made from a solid ferrite magnet. When the magnet band is worn on the wrist, the wrist is subjected to a magnetic field, which affords improved blood circulation and produces a therapeutic effect on stiff shoulders and pains. Thus the device gives an indirect efficacy only. It has therefore been desired to provide a magneto-therapeutic device with a magnetic field which will act directly on the affected part of the body to achieve enhanced therapeutic effectiveness.

For the same therapeutic uses as described above, devices are also known which comprise a base member of wood or synthetic resin and a permanent magnet embedded in the base member or which comprise an adhesive plaster incorporating magnetic particles, but the devices of the former type are not usable for a prolonged period of time or at all times, whereas those of the latter type have the drawbacks of having no pressure-stimulation effects, possessing weak magnetism and being unable to apply the magnetism concentrically to effective spots or affected part of the human body.

OBJECTS OF THE INVENTION

An object of the present invention is to provide a novel magneto-therapeutic device.

Another object of the invention is to provide a magneto-therapeutic device comprising a hard disc-shaped permanent magnet of ferrite and capable of achieving improved therapeutic efficacies on stiffness in the shoulder and pains in the waist, muscles and the like by concentrating the magnetic effects and pressure-stimulation effects of the magnet directly on the affected part or effective spots of the human body.

Still another object of the invention is to provide a magneto-therapeutic device which is easy to handle and usable for a prolonged period of time.

These and other objects of the invention will become apparent from the following description with reference to the accompanying drawings.

DETAILED DESCRIPTION

The present inventor has found that the foregoing objects can be readily fulfilled by providing a magneto-therapeutic device comprising an adhesive base sheet, a hard disc-shaped permanent magnet of ferrite having a magnetic field with an intensity of 500 to 1,000 oersteds and adhered to the base sheet in the center of its adhesive face, and a release sheet affixed to the adhesive face of the base sheet except the center portion thereof.

Figure 1:
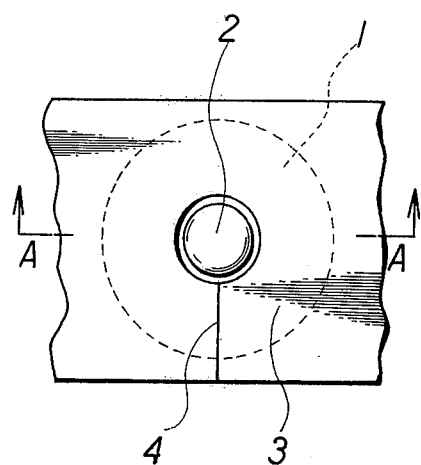
FIG. 1 is a plan view showing a magneto-therapeutic device embodying the present invention.
Figure 2:
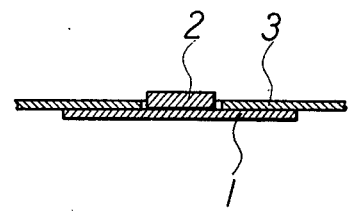
FIG. 2 is a view in section taken along the line A—A in FIG. 1.

With reference to the drawings, embodiments of the present invention will be described below. FIGS. 1 and 2 show a circular adhesive plaster or like adhesive base sheet 1, a hard disc-shaped ferrite permanent magnet 2 adhered to the base sheet 1 in the center of its adhesive face, and a release sheet 3 affixed to the adhesive face of the base sheet 1 except the center portion thereof. The release sheet 3 has a cut portion 4. The hard disc-shaped permanent magnet 2 measures, for instance, about 5 mm. in diameter and about 2.5 mm. in thickness and has a flat top face. The magnetic field of the magnet 2 has an intensity of about 500 to about 1,000 oersteds. The above-mentioned size of the permanent magnet 2, about 5 mm. in diameter and about 2.5 mm. in thickness, is determined by fulfilling, to the best advantage, the requirement that the area of contact between the magnet and the human body be reduced to the greatest possible extent within an allowable limit to ensure increased pressure-stimulation effects and the opposing requirement that the contact area be maximized within a permissible range to assure the effective magnetic function of the magnet. The release sheet 3 serves to protect the adhesive face of the base sheet 1 from staining until the device is placed into use. Suitable materials for the release sheet 3 are paper, cellophane and polyethylene or like film. The cut portion 4 is provided to facilitate the removal of the release sheet 3 for use.

For application, the release sheet 3 is removed from the present device and the device is then affixed to a painful or stiff portion or an effective spot of the body. The device will produce the following effects. When the device is applied to the human body through which the blood and body fluid are flowing, a magnetic field acts on the portion where the device is applied, creating an electromotive force which in turn generates an electric current. Consequently ions are liberated within the body, breaking the equilibrium established between the electrolyte and ions in the body, and an ionization tendency will result. This produces an influence mainly on the autonomic nervous system, eventually leading to improved blood circulation to ease stiffness in the muscle. In this way, the hard disc-shaped permanent magnet of ferrite, affixed directly to an affected portion or effective spot, gives a pressing stimulus thereto and produces a magnetic field thereon and therefore affords enhanced therapeutic effects. Since the base sheet has a size, e.g. a diameter of about 20 mm., suitable for holding the disc-shaped permanent magnet, the device is very convenient to handle.

Figure 3:
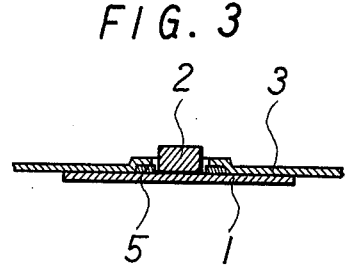
FIG. 3 is a sectional view showing another magneto-therapeutic device embodying the invention.

FIG. 3 shows another embodiment of the invention in section. The illustrated embodiment includes a pad 5 made from foamed synthetic resin, such as polystyrene, in the form of a doughnut and adhered to the center of an adhesive base sheet 1, with a hard disc-shaped ferrite permanent magnet 2 fitting in the inner periphery of the pad 5. Whereas an adhesive sheet or plaster, when applied to the body, may possibly make the plastered portion itchy, the provision of the pad 5 serves to reduce the area of contact between the body and the adhesive base sheet 1, thus mitigating such a side effect.

Figure 4:
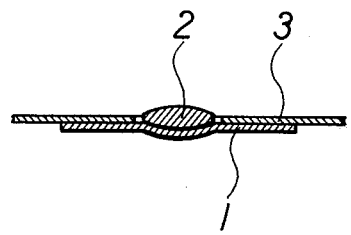
FIG. 4 is a sectional view showing another magneto-therapeutic device embodying the invention.

FIG. 4 shows still another embodiment of the invention in section comprising a hard disc-shaped ferrite permanent magnet 2 having a convex top face. In the case of such a magnet 2, lines of magnetic force concentrate in the center of its top face, giving a higher magnetic flux density, i.e. an increased magnetic force, to the affected part or effective spot of the human body. Accordingly the permanent magnet 2 exerts magnetic effects concentrically on the affected part or effective spot to achieve an enhanced therapeutic efficacy. In addition, the permanent magnet of the shape described feels soft and yet gives improved pressure-stimulation effects.

Figure 5:
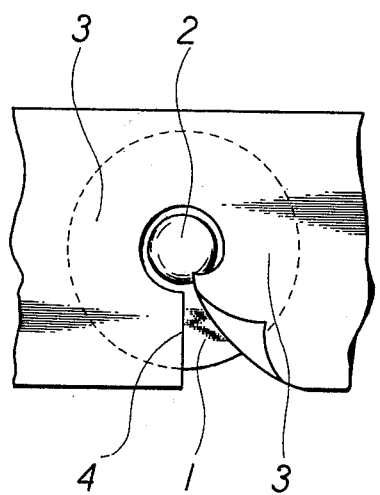
FIG. 5 is a view illustrating the device of the invention while a release sheet is being peeled off therefrom.

FIG. 5 shows the magneto-therapeutic device of the invention while the release sheet 3 is being peeled off the adhesive base sheet 1. As is illustrated, the cut portion 4 formed in the release sheet 3 greatly facilitates the removal of the release sheet 3 for the application of the device.

Figure 6:
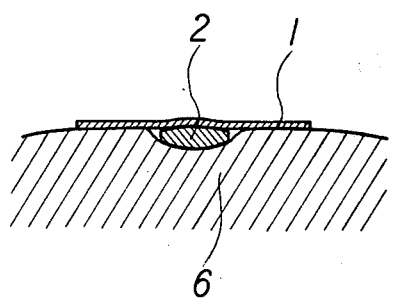
FIG. 6 is a sectional view illustrating the device of the invention while it is applied to the human body.

FIG. 6 is illustrating the device of the present invention while it is applied to the human body. As is illustrated, the hard disc-shaped ferrite permanent magnet 2 which is embedded in the skin of the human body 6, exerts pressure-stimulation effects and magnetic effects there about.

The hard disc-shaped permanent magnet of ferrite used in the device of the present invention is prepared from ferrite particles comminuted to a size of about 1 micron by molding the particles to the desired dimensions and shape at pressure of about 1 ton/cm². and sintering the molded piece at about 1,200° C. The hard disc-shaped permanent magnet thus prepared is as high as 500 to 1,000 oersteds in the intensity of its magnetic field, free of demagnetization and corrosion, lightweight, inexpensive to make and suited to quantity production.

When the side of the hard disc-shaped ferrite permanent 2 which contacts with the adhesive base sheet 1 is magnetized as the N-pole, the opposite side, i.e. the side which contacts with the human body is the S-pole. The converse as to the magnetic pole is also adoptable.

For ease of handling, a plurality of the present devices may be made available as a set, for instance, ten in two rows, as affixed to a release sheet having perforations for the magnetic discs. A number of such sets can be stored conveniently in layers if the permanent magnets are all arranged with the same side exposed, for instance, with the N-pole side adapted for contact with the human body.

As described above, the magneto-therapeutic device of the pressent invention is simple in construction and easy to handle and produces enhanced therapeutic effects, for instance, on stiffness in the shoulder with the magnetic and pressure stimuli given by the hard disc-shaped ferrite permanent magnet in direct contact with an effective spot or affected part of the body.

The present invention will be described in greater detail with reference to the following Example.

EXAMPLE

Magneto-therapeutic devices were prepared according to the present invention, each comprising a sheet of adhesive plaster 20 mm. in diameter, a hard disc-shaped permanent magnet of ferrite (5 mm. in diameter and 2.5 mm. in thickness, with a convex top face as illustrated in FIG. 4) having a magnetic field of about 600 oersteds in intensity and adhered to the plaster sheet in the center of its adhesive face, and a release sheet affixed to the adhesive face of the plaster sheet except the center portion thereof.

The devices were used by 30- to 70-year-old patients with the symptoms listed in Table 1 below to test the devices for therapeutic effects.

Table 1

| Symptom | Number of patients |
| --- | --- |
| Stiffness in shoulder | 338 |
| Lumbago | 47 |
| Neuralgia | 58 |
| Myalgia | 47 |

The device was separated from the release sheet, held affixed to the painful spot of the patient for 6 days and checked for its therapeutic effects. The results are given in Table 2 below.

Table 2

| | Number of patients | | | |
| --- | --- | --- | --- | --- |
| | Stiffness in shoulder | Lumbago | Neuralgia | Myalgia |
| Effective | 322 | 45 | 55 | 43 |
| Ineffective | 2 | 0 | 0 | 1 |
| No answer | 14 | 2 | 3 | 3 |
| Total | 338 | 47 | 58 | 47 |

The patients who found the device effective were checked for when the effect appeared (to be referred to simply as "time" below), with the results given in Table 3.

Table 3

| | Number of patients | | | |
| --- | --- | --- | --- | --- |
| Time | Stiffness in shoulder | Lumbago | Neuralgia | Myalgia |
| After a few hours | 69 | 6 | 1 | 7 |
| After one day | 94 | 10 | 14 | 9 |
| After two day | 95 | 15 | 13 | 18 |
| After three day | 47 | 5 | 14 | 4 |
| After four day | 17 | 9 | 13 | 5 |
| Total | 322 | 45 | 55 | 43 |

None of the patients using the device felt itchy or had a rash, while many found that intercurrent headache, arthritis, rheumatism or the like was also cured.

What is claimed is:

1. A magneto-therapeutic device comprising an adhesive base sheet, a hard disc-shaped permanent magnet of ferrite having a convex top face, a diameter of about 5 mm and a thickness at its center of about 2.5 mm and having a magnetic field of 500 to 1,000 oersteds in intensity and adhered to the base sheet in the center of its adhesive face, and a release sheet affixed to the adhesive face of the base sheet except the center portion thereof.

2. The magneto-therapeutic device of claim 1, wherein said adhesive base sheet is a circular sheet of adhesive plaster having a diameter of about 20 mm.

3. The magneto-therapeutic device of claim 1, wherein said release sheet has a cut portion.

* * * * *